US006689760B1

(12) United States Patent
Yatvin et al.

(10) Patent No.: US 6,689,760 B1
(45) Date of Patent: Feb. 10, 2004

(54) ANTI-MYCOBACTERIAL COMPOSITIONS

(75) Inventors: Milton B. Yatvin, Portland, OR (US); Richard L. Pederson, San Gabriel, CA (US)

(73) Assignee: EnzRel Inc., Portland, OR (US)

( * ) Notice: Subject to any disclaimer, the term of this patent is extended or adjusted under 35 U.S.C. 154(b) by 0 days.

(21) Appl. No.: 09/613,409

(22) Filed: Jul. 10, 2000

(51) Int. Cl.$^7$ ............................................... A61K 31/70
(52) U.S. Cl. ........................ 514/45; 514/47; 536/26.24
(58) Field of Search ........................ 536/26.24; 514/45, 514/47

(56) References Cited

U.S. PATENT DOCUMENTS

| | | | |
|---|---|---|---|
| 4,744,989 A | 5/1988 | Payne et al. |
| 4,921,757 A | 5/1990 | Wheatley et al. |
| 4,963,526 A | 10/1990 | Ecanow et al. |
| 5,004,611 A | 4/1991 | Leigh |
| 5,043,165 A | 8/1991 | Radhakrishnan |
| 5,053,217 A | 10/1991 | Lehigh |
| 5,141,674 A | 8/1992 | Leigh |
| 5,223,263 A | 6/1993 | Hostetler et al. |
| 5,466,468 A | 11/1995 | Schneider et al. |
| 5,484,809 A | 1/1996 | Hostetler et al. |
| 5,580,571 A | 12/1996 | Hostetler et al. |
| 5,610,163 A | 3/1997 | Banholzer et al. |
| 5,626,869 A | 5/1997 | Nygvist et al. |
| 5,635,206 A | 6/1997 | Ganter et al. |
| 5,654,314 A | 8/1997 | Banholzer et al. |
| 5,665,379 A | 9/1997 | Herslof et al. |
| 5,744,461 A | 4/1998 | Hostetler et al. |
| 5,744,592 A | 4/1998 | Hostetler et al. |
| 5,756,116 A | 5/1998 | Hostetler et al. |
| 5,762,904 A | 6/1998 | Okada et al. |
| 5,770,738 A | 6/1998 | Banholzer et al. |
| 5,843,509 A | 12/1998 | Calvo Salve et al. |
| 5,955,451 A | 9/1999 | Lichtenberger et al. |
| 5,958,450 A | 9/1999 | Tashiro et al. |
| 6,015,576 A | 1/2000 | See et al. |
| 6,060,082 A | 5/2000 | Chen et al. |
| 6,117,449 A | 9/2000 | See et al. |
| 6,207,185 B1 | 3/2001 | See et al. |
| 6,231,888 B1 | 5/2001 | Lerner et al. |

FOREIGN PATENT DOCUMENTS

| | | |
|---|---|---|
| EP | 350287 | 1/1990 |
| EP | 855179 | 7/1998 |
| WO | WO 89/02733 | 4/1989 |
| WO | WO 93/00910 | 1/1993 |
| WO | WO 95/030035 | 2/1995 |
| WO | WO 99/07699 | 2/1999 |

OTHER PUBLICATIONS

Rozwarski et al., Science, vol. 279, pp. 98–102, Jan. 2, 1998.*
Alvarez–Dominquez et al., 1993 Infect Immun 61:3664–3672.
Bignami et al., 1992 Cancer Res 52:5759–5764.
Embretson et al., 1993 Nature 362:359–362.
Gregoriadis. 1995, Trends in Biotechnology 13:527–537.
Kanno et al 1993, J. Virol 67:2075–2082.
Kanno et al., 1992, J. Virol 66:5305–5312.
Katare et al., 1991 J. Microencapsulation 81:1–7.
Kulkarne et al., 1995, Pharm. Sci. 1:359–362.
Ledley, 1995 Human Gene Therapy 6:1129–1144.
Maciejewski et al., 1993, Virol 195:327–336.
Manusama et al., 1998 Semin Surg. Oncol. 14:232–237
Meltzer & Gendelma, 1992, Curr. Top. Microbiol Immunol 181:239–263.
Mickisch 1995 World J. Urology 13:178–185.
Rahnam et al., 1982 Life Sciences 31:2061–71.
Sierra–Honigman et al., 1993 J. Neuroimmunal 45:31–36.
Storm & Crommetin, 1997, Hybridon 16:119–125.
Sturgill–Koszycki et al. 1994, Science 263:678–681.
Yang et al., 1997, J. Neurotrauma 14:281–297.
Tono–Oka, (1982) Bull. Chem. Soc. Jpn., 55, 1531–1537.*
S. Tono–Oka, "Enzymatic synthesis of pyridine nucleotides. Structural propert of some new NAD–analogs, and base conditions available for the analog formation", Bull. Chem. Soc. JPN., vol. 55, 1982, pp. 1531–1537.
E.A. Vorontsov et al., "Reaction of lactate dehydrogenase with 3–acetylpyridine adenin dinucleotide", Sov. J. Bioorg Chem., vol. 2, No. 7, 1976, pp. 718–724.
S.R. Bolsover et al., "From genes to cells" 1997, Wiley, New York p. 254.
D.A. Rozwarski et al., "Modification of NADH of the isoniazid target (InhA) from Mycobacterium tuberculosis", Science, vol. 279, 1998, pp. 98–102.
Angew. Chem. Int. Ed., vol. 38,1999, pp. 2588–2590.

* cited by examiner

*Primary Examiner*—James O. Wilson
(74) *Attorney, Agent, or Firm*—McDonnell Boehnen Hulbert & Berghoff

(57) ABSTRACT

This invention provides compositions of matter, pharmaceutical compounds, methods of synthesizing such compounds and methods for using such compounds to treat animals infected with a pathogenic mycobacterium. The invention specifically provides compositions and pharmaceutical compositions thereof for the treatment of tuberculosis and other Mycobacterium-caused diseases.

17 Claims, 13 Drawing Sheets

ANTI-MYCOBACTERIAL COMPOSITIONS

BACKGROUND OF THE INVENTION

1. Field of the Invention

This invention relates to compositions of matter, pharmaceutical compounds, methods of synthesizing such compounds and methods for using such compounds to treat animals infected with a pathogenic microorganisms, specifically mycobacteria. The invention relates in particular to compositions of matter and pharmaceutical compositions thereof for the treatment of tuberculosis and other Mycobacterium-caused diseases.

2. Background of the Related Art

Tuberculosis is a human disease caused by infection with *Mycobacterium tuberculosis*. This disease typically arises after inhalation in phagocytic macrophages in the lung, where characteristic localized sites of infection (termed tubercules) are formed and comprise sites of further systemic infection. Although previously well-controlled by antibiotics such as isoniazid, the development of drug-resistance by the infectious agent, and the increased numbers of immune-compromised individuals being affected by the AIDS crisis has created a near epidemic of tuberculosis cases world-wide. In 1997, the World Health Organization reported tuberculosis to be the world's top infectious killer.

About one-third of new tuberculosis cases are resistant to the current drug-treatment regimes. It is estimated that drug-resistant tuberculosis accounts for between 2% and 14% of total tuberculosis cases worldwide. As tuberculosis is spread by air-borne droplets from coughing by infected individuals, and its spread is further facilitated in crowded environments such as cities, there is a great potential for a precipitous increase in tuberculosis infections which will not be easily controlled by conventional medicinal intervention, such as isoniazid administration. Lethal strains of tuberculosis have the potential for rapid spread, since only about one in ten patients receives the medical treatment necessary to contain and successfully treat the disease. Thus, there exists in this art a need to develop new and better treatments for tuberculosis, particularly tuberculosis infections resistant to traditional antibiotic treatments.

There is also a need in the art for more effective anti-tuberculosis drugs to which *M. tuberculosis* is not resistant and, most advantageously, drugs having a low resistance development potential.

In addition, there are a number of other human and animal diseases caused by mycobacteria, including for example leprosy (Hansen's disease), lymphadenitis, a variety of pulmonary and skin diseases, and wound infection. Although less prevalent, each of these diseases is associated with morbidity, mortality and economic costs such as lost production time and the cost of medical treatment. Resistance to drugs used heretofore to control and treat such diseases is also a current problem, thus raising a further need in this art for more effective drugs against many different Mycobacterium species.

SUMMARY OF THE INVENTION

The present invention is directed to improved antibiotic compounds, specifically pharmaceutical compositions thereof, and methods for producing and administering such pharmaceutical compositions, for treatment of diseases having a Mycobacterium etiology. In particular, the invention is directed towards delivery of antimicrobial compounds, drugs and agents specific for treatment of tuberculosis and other Mycobacterium-caused diseases in humans.

The invention provides improved antimycobacterial drugs that are "activated" embodiments (as defined herein) of competitive, non-competitive and "suicide substrate" inhibitors of long chain enol-acyl carrier protein reductase (InhA), a Mycobacterium-specific enzyme necessary for the production of mycolic acid, which an essential component of the mycobacterial cell wall. Inhibition of this enzyme by isoniazid is the basis of current anti-tuberculosis treatment modalities, and resistance to isoniazid is the principle form of drug resistance exhibited by mycobacteria. The compounds of the invention overcome resistance by being "pre-activated", i.e., these compounds do not rely on activation in the mycobacterium-infected cell for activity (unlike isoniazid itself). Thus, it is expected that resistance is less likely to be developed against these drugs. In a preferred embodiment, these compounds have the generic structure:

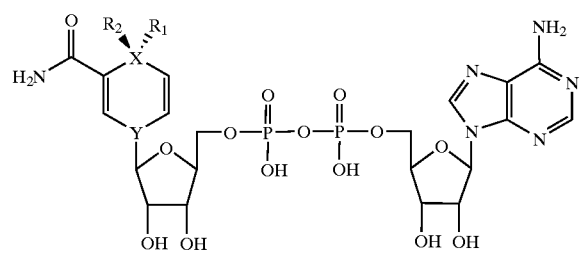

wherein X can be C or O; Y can be N or C; $R^1$ and R2 can each be independently an electron pair, H, $CH_3$, $CH_2$—$CH_3$, or $O(CH_2)_3O$ or together can be =O, =$CH_2$, —$CH_2$—$CH_2$—, =CH—CH=$CH_2$, =CH—COO$CH_2$—$CH_3$, or $OCH_2$.

Each of the compounds disclosed herein is an analog for nicotinamide adenine dinucleotide, a cellular component that mediates transfer of electrons in a number of cellular systems (including glycolysis, mitochondrial oxidative phosphorylation, fatty acid synthesis and breakdown, and other synthetic and metabolic pathways). It is known in the art that isoniazid, the traditional drug of choice for treating tuberculosis, is activated by a *M. tuberculosis* produced catalase/peroxidase (as shown in FIG. 1); Quemard et al., 1996, *J. Amer. Chem. Soc.* 118: 1561; Sacchettini & Blanchard, 1996, *Res. Microbiol.* 147: 36; Zabinski & Blanchard, 1997, *J. Amer. Chem. Soc.* 119: 2331) to form an adduct with NAD (the resulting activated form of isoniazid is termed isoniazid-NAD analogue (INA); Rozwarski et al., 1998, *Science* 279: 98-102). A major route for isoniazid resistance to *M. tuberculosis* is mutation or inactivation of the catalase/peroxidase that converts isoniazid to INA, suggesting that mycobacteria may be less likely to develop resistance to INA that to isoniazid itself.

A major drawback for using INA directly to treat *M. tuberculosis* infections is that INA is expected to inhibit a variety of NAD-dependent host enzymes, with toxic or at least deleterious effects. In one embodiment of the invention, this limitation is overcome by providing alternative embodiments of INA that have been derivatized at one or more positions on the molecule required for enzyme binding. Both the formamide group of NAD and the adenine portion thereof bind to amino acid sequences in the NAD binding portion of NAD requiring enzymes that have been highly conserved in evolution (Rossman et al., 1978, *Molec. Cell. Biochem.* 21: 161–182; Baker et al., 1992, *J. Molec. Biol.* 228: 662–671; Zeng et al., 1995, *Biochem. J.* 310:

507–516). Modification of INA at either position disrupts binding to NAD-requiring enzymes.

In order to specifically target *M. tuberculosis* and other Mycobacterium-infected cells with an activated form of INA, most preferably phagocytic cells known to be in vivo reservoirs of Mycobacterium infection, inactivating modifications thereof are made using derivatizing groups that are specifically cleaved in Mycobacterium-infected cells. In a preferred embodiment, the derivatizing group is a urea moiety, because Mycoabacteria produce urease in infected cells that can cleave the urea group from the derivatized INA analogue and thus activate INA in such cells (Wayne and Kuica, 1986, BERGEY'S MANUAL OF SYSTEMIC BACTERIOLOGY (Sneath et al., eds.), Williams & Wilkins; Good et al., 1985, *Ann. Rev. Microbiol.* 39: 347). Preferred positions for derivatizing INA with said urea moieties include the formamide group of the pyridine portion of the NAD component of INA, and the 1-amino group of the adenine portion of NAD component of INA. Because mammalian cells not infected with Mycobacteria do not produce urease, the modified INA compounds of the invention do not have toxic or deleterious effects on such cells.

Particularly preferred targets of the pharmaceutical compositions of the invention are phagocytic cells, preferably macrophages and phagocytic neutrophiles and most preferably macrophages, mononuclear cells and phagocytic neutrophiles from lung tissue that are infected with *M. tuberculosis, M. africanum, M. bovis* or any other microorganism that causes tuberculosis in an animal, most preferably a human. Also preferred targets are cells infected with *M. leprae, M. avium, M. intracellulare, M. scrofulaceum, M. kansasii, M. xenopi, M. marinum, M. ulcerans, M. fortuitum* and *M. chelonae*.

The anti-mycobacterial compounds of the invention are advantageous because, inter alia, the compounds are "activated" inhibitors of a target enzyme specific for mycobacterial cells. Inhibition of this enzyme is unlikely to be disadvantageous to infected animals, since there is no eukaryotic or vertebrate analogue of this enzyme. In addition, the anti-mycobacterial compounds and pharmaceutical compositions thereof are provided in a prodrug form that is inactive in uninfected cells but is specifically activated in cells, most preferably phagocytic cells, infected to Mycobacteria species.

The invention provides a method of killing a microorganism infecting a mammalian cell, preferably a phagocytic mammalian cell. This method comprises contacting an infected phagocytic mammalian cell with the compositions of matter or pharmaceutical compositions of the invention in vivo or in vitro. The invention also provides methods for treating microbial infections in an animal, most preferably a human wherein the infecting microbe is present inside a phagocytic cell in the human, the method comprising administering a therapeutically effective amount of the compositions of matter or pharmaceutical compositions of the invention to the human in a pharmaceutically acceptable carrier. Thus, the invention also provides pharmaceutical compositions comprising the compositions of matter of the invention in a pharmaceutically acceptable carrier. In a preferred embodiment, the pharmaceutical composition is formulated in an orally-administered dose. In most preferred embodiments, the infecting microorganism is a tuberculosis-causing microorganism such as *M. tuberculosis, M. africanum* or *M. bovis*.

Specific preferred embodiments of the present invention will become evident from the following more detailed description of certain preferred embodiments and the claims.

DETAILED DESCRIPTION OF THE PREFERRED EMBODIMENTS

The present invention provides compositions of matter, pharmaceutical compositions and methods of use thereof for treatment of mycobacterium-associated diseases and disorders in an animal. For the purposes of this invention, the term "mycobacterium" is intended to encompass all pathogenic or disease-causing microorganisms, most preferably tuberculosis-causing microorganisms including but not limited to *M. tuberculosis, M. africanum, M. bovis, M. leprae, M. avium, M. intracellulare, M. scrofulaceum, M. kansasii, M xenopi, M. marinum, M. ulcerans, M. fortuitum* and *M. chelonae*.

Figure 2:
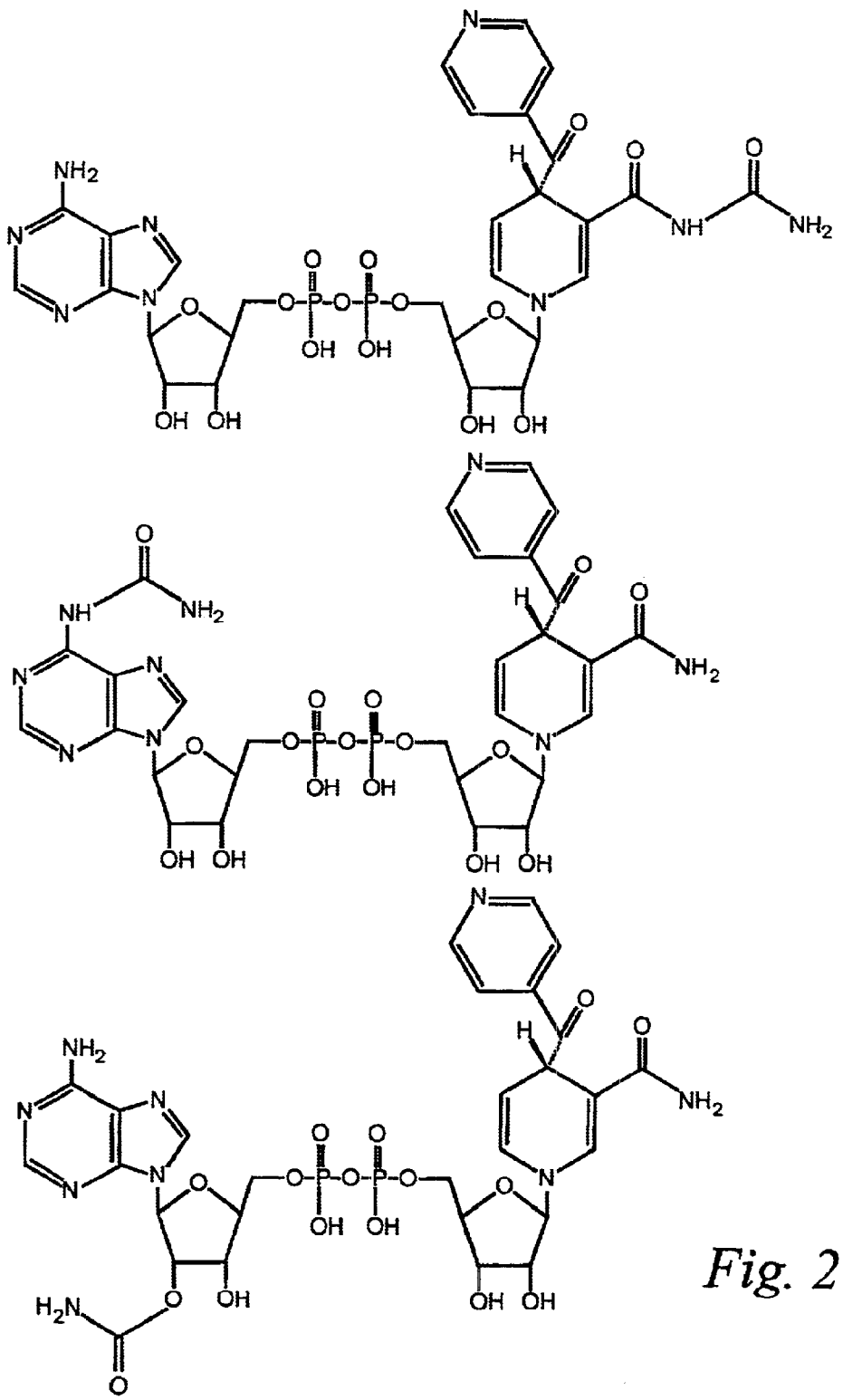
FIG. 2 is a schematic representation of exemplary prodrugs according to the invention.
Figure 3:
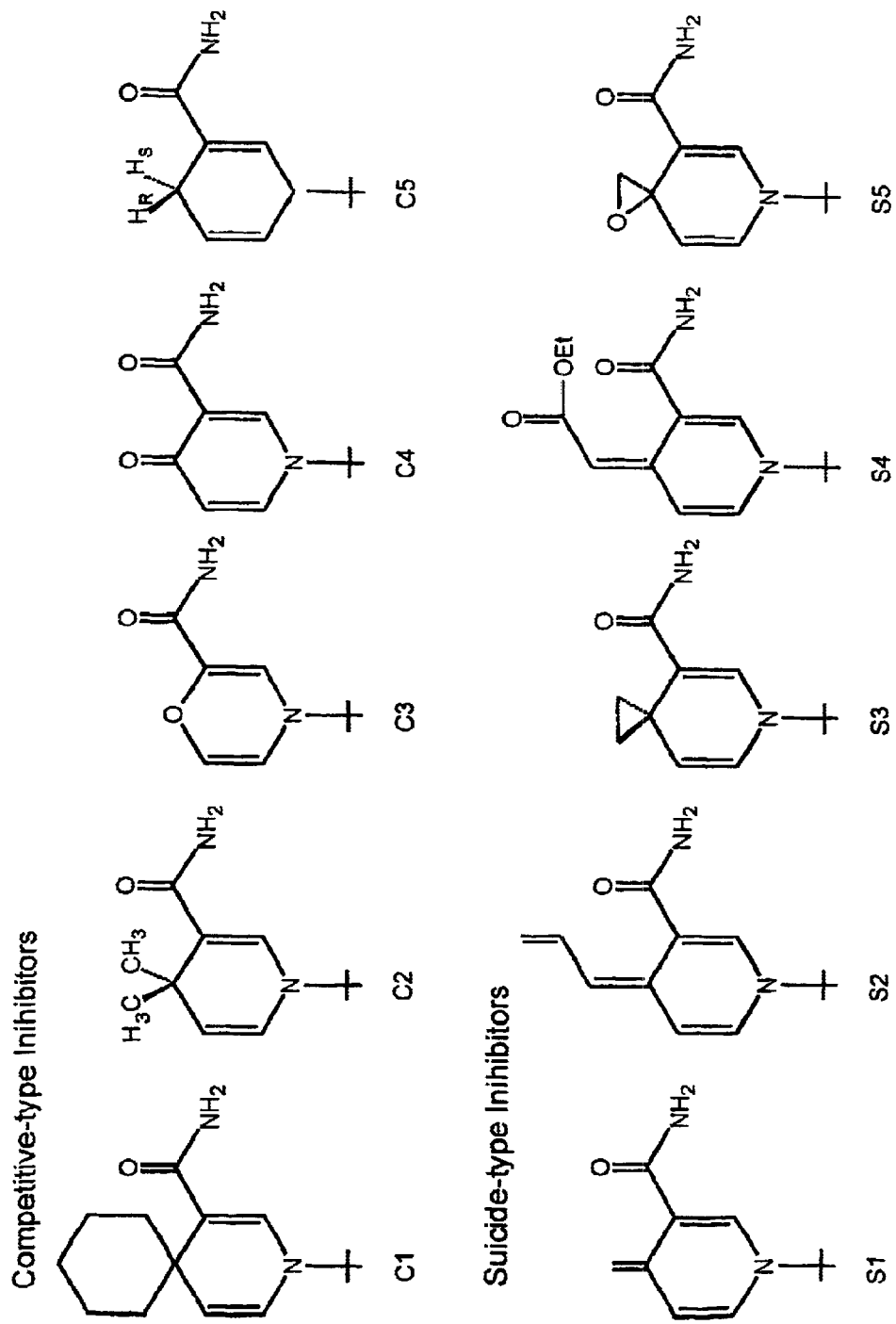
FIG. 3 depicts competitive and suicide substrates of InhA.

The compounds of the invention include but are not limited to all varieties of drugs or agents, particularly antibiotic and antimicrobial drugs, and most preferably anti-tuberculosis drugs and agents, having a cytotoxic or cytostatic effect on mycobacterium growth and proliferation, including but not limited to competitive, non-competitive and "suicide substrate" InhA inhibitors. Preferred embodiments of the specific compounds provided by the invention are shown in FIGS. 2 and 3. In most preferred embodiments, the invention provides modified embodiments of isoniazid-NAD analogue (INA) that is the activated form of the conventional anti-tuberculosis drug, isoniazid.

Figure 1:
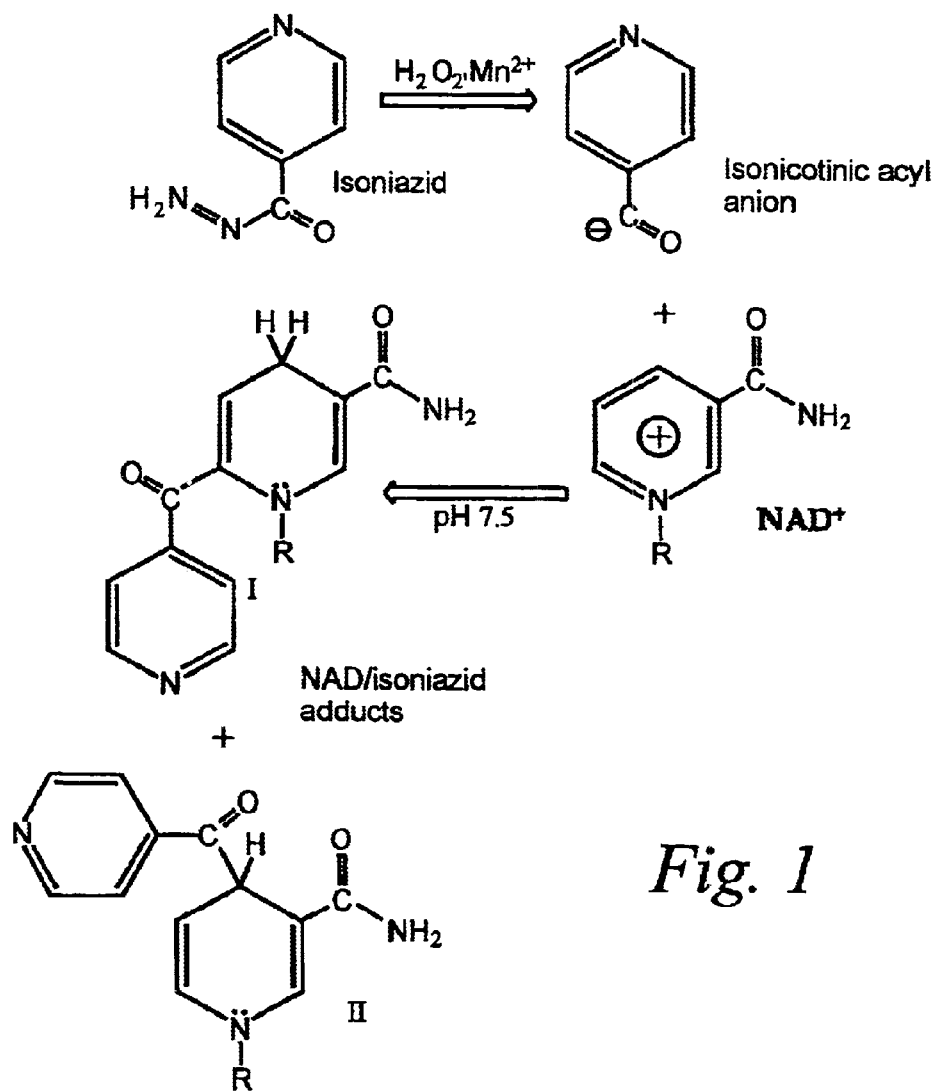
FIG. 1 is a diagram showing activation of the anti-tuberculosis drug isoniazid.

Without being limited to any theory explaining the action of the anti-mycobacterial compounds provided by the invention, it will be understood that a requirement for mycobacterial cell growth is the production of mycolic acid, a critical component of the *M. tuberculosis* cell wall. Inhibition of mycolic acid production is the molecular basis of isoniazid anti-tuberculosis activity, since mycolic acid is neither required or produced by eukaryotic, particularly animal, cells. Thus, an established clinical target for anti-mycobacterial treatment is disrupting mycolic acid production. An illustration of this is shown in FIG. 1. In the Figure, the anti-tuberculosis drug isoniazid is activated by reaction with the oxidized form of nicotinamide adenine dinucleotide (NAD+) to form the activated form of isoniazid (INA) that inhibits long chain enol-acyl carrier protein reductase (IhA), an enzyme needed for synthesis of mycolic acid.

A limitation of such therapy, however, is the development of drug resistance by the mycobacterium. This phenotype is frequently expressed by as loss-of-function mutation involving a mycobacterially-encoded catalase/-peroxidase that prevents activation of isoniazid to the active adduct shown in FIG. 1. Without mycobacterial-mediated activation, the drug loses its anti-mycobacterial properties.

The present invention overcomes the capacity of mycobacteria to develop resistance by providing NAD analogues that are "preactivated" and require no further activation from the mycobacteria. Delivery of the compounds of the invention is itself sufficient to inhibit InA, and thus having an antimycobacterial effect.

In preferred embodiments, the activated isoniazid-NAD analogues of the invention are provided in a form that is inactive in a mammalian, most preferably a human, cell not infected with mycobacteria. In these embodiments, the analogue, most preferably INA, is derivatized at a conserved position in the NAD molecule involved in NAD binding to NAD-requiring enzymes. Most preferably, such positions include but are not limited to the formamide group of the pyridine portion of the NAD component of INA, and the 1-amino group of the adenine portion of the NAD component of INA. Derivatives containing blocking groups at these positions are severely inhibited (by at least about 10-fold in binding affinity) in binding to NAD-requiring enzymes.

Specific, targeted activation of such derivatized activated isoniazid analogues in cells, preferably mammalian cells, more preferably human cells and most preferably phagocytic cells, is achieved according to the invention by providing derivatized activated analogues wherein the derivatizing group is specifically cleaved in mycobacterium-infected cells. In one aspect, such specific cleavage is due to an chemical linkage in the derivative that is labile within the infected cell due to conditions caused by or that result from infection of the cell with the mycobacteria. In another preferred aspect, such specific cleavage is due to an enzymatic activity which is produced either by the mycobacteria itself or by the cell as the result of infection with said mycobacteria, wherein the linkage is enzymatically cleaved by the enzymatic activity. In particularly preferred embodiments, the derivatizing group is a urea moiety that is specifically cleaved in Mycobacteria-infected cells by a mycobacteria-encoded urease.

The terms "anti-mycobacterial drug, anti-tuberculosis drug or anti-Mycobacterium drug" is intended to encompass any pharmacological agent effective in inhibiting, attenuating, combating or overcoming infection of phagocytic mammalian cells by a tuberculosis-causing or other disease-causing Mycobacterium species microbial pathogen in vivo or in vitro. Anti-tuberculosis drugs as provided by the invention include but are not limited to competitive, non-competitive and "suicide substrate" InhA inhibitors as disclosed herein, most preferable prodrug forms of the activated form of isoniazid, INA as disclosed herein. Activated and prodrug embodiments of these or other antibiotic, antimicrobial or antiviral compounds, drugs or agents are also preferred.

The antimycobacterial, anti-tuberculosis or anti-Mycobacterium compounds, drugs or agents of this invention are useful in inhibiting, attenuating, arresting, combating and overcoming infection of phagocytic mammalian cells by pathogenic microorganisms in vivo and in vitro, particularly tuberculosis-causing species such as *M. tuberculosis, M. africanum* and *M. bovis*, as well as infection by *M. leprae, M. avium, M. intracellulare, M. scrofulaceum, M. kansasii, M. xenopi, M. marinum, M. ulcerans, M. fortuitum* and *M. chelonae*. To this end, the invention provides methods for treating an animal having a disease or disorder caused by one of these microorganisms, wherein the antimycobacterial, anti-tuberculosis or anti-Mycobacterium compounds, drugs or agents of this invention are administered to an animal infected with a pathogenic microorganism that acutely or chronically infects phagocytic mammalian cells. In addition, prophylactic embodiments and uses of the pharmaceutical compounds of the invention are provided, for inoculating vulnerable phagocytic cells prior to or roughly coincident with infection with a pathological or disease-causing microorganism. The antimycobacterial, anti-tuberculosis or anti-Mycobacterium compounds, drugs or agents of this invention for prophylactic or therapeutic uses are administered in a dosage and using a protocol sufficient to have an antimicrobial effect in the phagocytic cells of the animal. In addition, pharmaceutical compositions useful in the methods of the invention are also provided, comprising antimycobacterial, anti-tuberculosis or anti-Mycobacterium compounds, drugs or agents of the invention and a pharmaceutically-acceptable carrier, adjuvant or excipient. Routes of administration include oral, ocular, buccal, intranasal, intravenous, intramuscular, parenteral, transdermal, and rectal. In particularly preferred embodiments, the pharmaceutical compositions of the invention are provided in an orally-administered dosage form, including formulations, excipients, binding agents and other features of tablets and other oral dosage forms known in the art. In additional preferred embodiments, the pharmaceutical compositions are provided as an aerosol or other easily-volatilized form, for delivery for example to the lung as provided by conventional inhalers and other pulmonary drug delivery devices and vehicles.

The following Examples illustrate certain aspects of the above-described method and advantageous results. The following examples are shown by way of illustration and not by way of limitation.

EXAMPLE 1

Preparing Activated Isoniazid Analogs

An activated isoniazid analog is prepared as described by Quemard et al. (1996, *J. Am. Chem. Soc.* 118: 1561–2). $^{14}$C-Isoniazid is incubated in the presence of H37R$_v$ enoyl-ACP reductase and katG-encoded catalase-peroxidase from wild type *M. tuberculosis* is incubated for 20 hours in a solution comprising 2 $\mu$M MgCl$_2$, 6% glycerol, 10 $\mu$M NADH, 100 $\mu$M isoniazid, 1.9 $\mu$M KatG and 9 $\mu$M NADH-specific enoyl-acyl carrier protein reductase (InhA). After incubation, the reaction mixture is applied to a Pharmcia-PD-10 column, eluted and analyzed by liquid scintillation counting. Only in the presence of catalase-peroxidase are significant amounts of $^{14}$C-labeled isoniazid observed to co-elute with wild type enoyl-ACP reductase. The *M. tuberculosis* katG-encoded catalase-peroxidase enzyme produces radicals in the presence of isoniazid and hydrogen peroxide (Hillar & Loewen, 1995, *Arch. Biochem. Biophys.* 323: 438–446.) The fractions having radioactivity are combined and dialyzed against water using a dialysis membrane having a 10,000 daltons molecular weight cut-off. The aqueous solution containing $^{14}$C-labeled isoniazid-NADH complex is lyophilized and the resulting white powder collected and characterized.

Alternatively, the method of Magliozzo et al. (1996, *J. Am. Chem. Soc.* 118: 11303–4) is used to produce an isoniazid-NADH analog. In this method, isoniazid (20 mM) is incubated for 3 hr in 0.015 M phosphate buffer (pH 7.0) containing 10 mM NADH and 130 $\mu$M manganese (II) nitrate. The Mn$^{+2}$ cation has been reported to catalyze the aerobic decomposition of isoniazid in a radical-mediated mechanism (Ito et al, 1992, *Biochemistry* 31: 11606–11613). The isoniazid-NADH analog is isolated by HPLC chromatography using 50 mM ammonium acetate (pH 7) and a 0% to 15% gradient of acetonitrile for elution. Fractions containing isoniazid-NADH analog are collected, concentrated and lyophilized to yield a powder.

EXAMPLE 2

Preparing Competitive and Irreversible Inhibitors of Long-chain Enol Acyl Carrier Protein Reductase Antimicrobial microparticles are produced comprising either competitive, non-competitive inhibitors or irreversible, "suicide substrate"-type inhibitors of long-chain enol acyl carrier protein reductase (InhA).

Competitive and irreversible inhibitors of ACP reductase are synthesized by modifying the nicotinamide ring of isoniazid and then using procedures described by Todd et al. (1950, *J. Am. Chem. Soc.* 303: 3272) to produce NAD analogs, as illustrated in FIG. 3.

The chemical synthesis of the competitive inhibitors uses 4-hydroxy-nicotinamide or cyclohexadiene as starting material. These NADH analogs prevent the synthesis of mycolic acid by mycobacteria and facilitate elimination of drug-resistant bacteria from infected persons.

1. Synthesis of 4-Oxo-2-formamide-dihydropyridine (C4-Int)

To a 100 mL round-bottomed flask was added 5 g (36.5 mmol) of 4-hydroxy-nicotinamide in 50 mL dichloromethane and cooled to −78° C. in a dry ice/acetone bath under a nitrogen atmosphere. Trifluoroacetic acid anhydride (19.1 g, 91.3 mmol), 6.2 g (73 mmol) dimethylsulfoxide (DMSO) and 20 mL triethylamine (Swem oxidation according to Huang et al., 1978, *Synthesis* p. 297; Ganem et al., 1974, *Tetrahedron Lett.* p. 917) were added at −78° C. and stirred for 2 h. The reaction was then warmed to room temperature overnight.

Figure 4A:
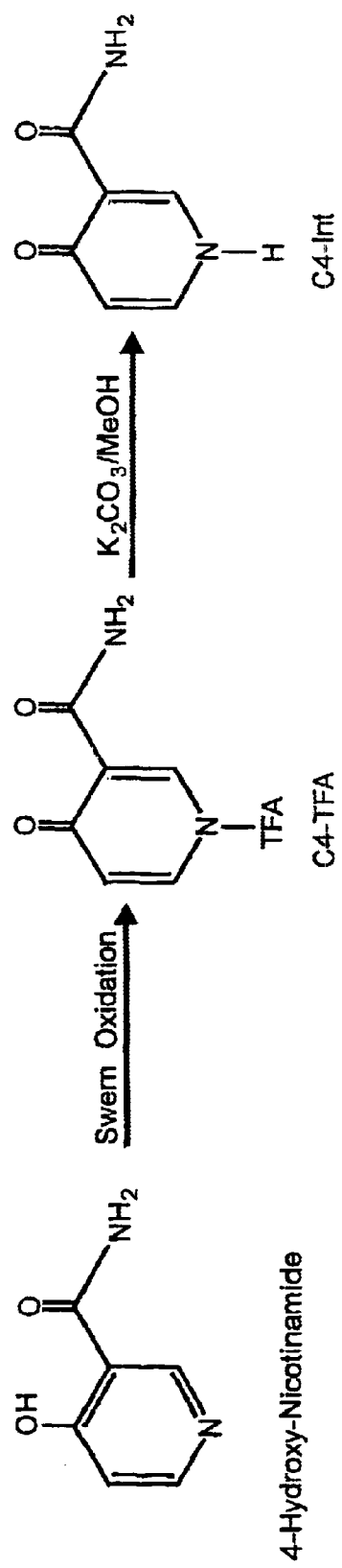
FIGS. 4A through 4J show the reaction schemes set forth in Example 2.

To the reaction mixture was added 50 mL crushed ice in water and stirred for 20 min. The aqueous and organic phases were then separated and the organic phase washed sequentially with 25 mL of a mixture of 1M HCl, water-saturated bicarbonate and brine. The methylene chloride layer was then dried over anhydrous sodium sulfate, filtered using Whatman #1 filter paper, concentrated under reduced pressure and purified by column chromatography using a 2 inch×24 inch glass column containing 100 g of silica gel (Fisher, 170 to 400 mesh). The product was eluted from the column with 10% ethyl acetate in hexanes to yield 6.3 g (27.4 mmol) of 4-oxo-2-formamide-N-trifluoroacetyl-dihydropyridine. The N-trifluoroacetyl group was removed by stirring in 50 mL of methanol, 1 mL of water and 2.74 g of potassium carbonate for 18 hr at room temperature. Excess potassium carbonate was removed by filtering through Whatman #1 filter paper and concentrated under reduced pressure to yield 3.4 g (25.4 mmol) of 4-oxo-2-formamide-dihydropyridine. This material was used in the following reactions without further purification. This synthesis is illustrated in FIG. 4A.

2. Synthesis of 4-Oxo-2-formamide-N-trimethylsilyl-dihydropyridine (C4-TMS)

Figure 4B:
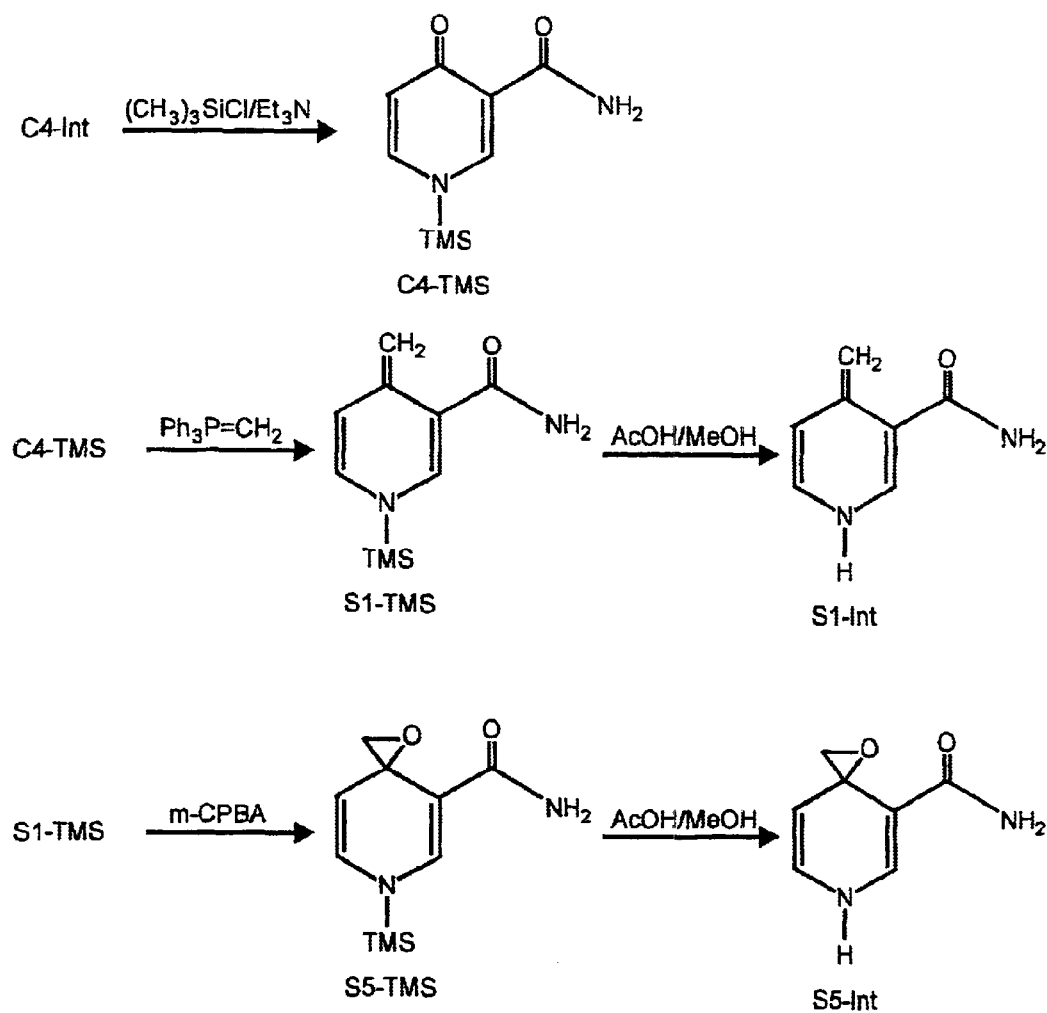

To a 50 mL round-bottomed flask was added 3 g (21.7 mmol) of C4-Int, 20 mL dichloromethane and 7.6 mL triethylamine. The mixture was cooled to −10° C. under a nitrogen atmosphere. Trimethylsilyl chloride (5.8 g, 54.5 mmol) in 10 mL dichloromethane was added slowly over about 1 h. The resulting triethylamine hydrochloride salt was removed by filtering and the organic phase washed with 10 mL cold 1M HCl and 10 mL cold water-saturated bicarbonate. The organic phase was then dried over anhydrous sodium sulfate, filtered as described above and concentrated under reduced pressure to yield 4.5 g (21.4 mmol) C4-TMS, which was used without further purification. This synthesis is illustrated in FIG. 4B.

3. Synthesis of Exo-4-methylene-2-formamide-dihydropyridine (S1-Int)

To a 50 mL round-bottomed flask was added 3 g (14.0 mmol) C4-TMS and 20 mL tetrahydrofuran (THF), and the mixture cooled to −10° C. under nitrogen atmosphere. The methylene Wittig reagent was prepared by the addition of 16.4 mL of 1 M (16.4 mmol) butyl lithium to 4.5 g (16.4 mmol) methyltriphenylphosphine bromide in 10 mL of THF at −10° C. for 1 hr; for examples of preparing Wittig reagents see Manabe et al., 1985, *Agric. Biol. Chem.* 49: 1205; Taylor et al., 1974, *J. Amer. Chem. Soc.* 96: 8095. The Wittig reagent was slowly added to the C4-TMS solution above over 15 minutes, and warmed to room temperature over an additional 3 h. Ether (20 mL) and 10 mL of a 0.5M HCl solution was added and the phases mixed and separated. The organic phase was dried over anhydrous sodium sulfate, filtered as described above, and purified by column chromatography as described above and eluted with 5% ethyl acetate in hexanes to yield 1.47 g (7.0 mmol) of exo-4-methylene 2-formamide-N-TMS dihydropyridine (S1-TMS). The TMS group was removed by stirring the product compound in a solution of 5% acetic acid in methanol for 8 hr at room temperature, and the extent of TMS removal monitored by TLC analysis (where S1-TMS has an $R_f$=0.6, and S1-Int, $R_f$=0.0 using 10% ethyl acetate in hexanes with ninhydrin as the visual indicator). After the cleavage reaction was complete, the product was concentrated under a 1 mm Hg vacuum for 12 h to remove excess acetic acid. The remaining golden syrup was triturated three times with 20 mL of ether, the ether fractions were combined and concentrated to yield 0.79 g (5.9 mmol) of exo-4-methylene 2-formamide dihydropyridine (S1-Int). This synthesis is illustrated in FIG. 4B.

4. Synthesis of Exo-4-(1',3'-butadiene) 2-Formamide Dihydropyridine (S2-Int)

Figure 4C:
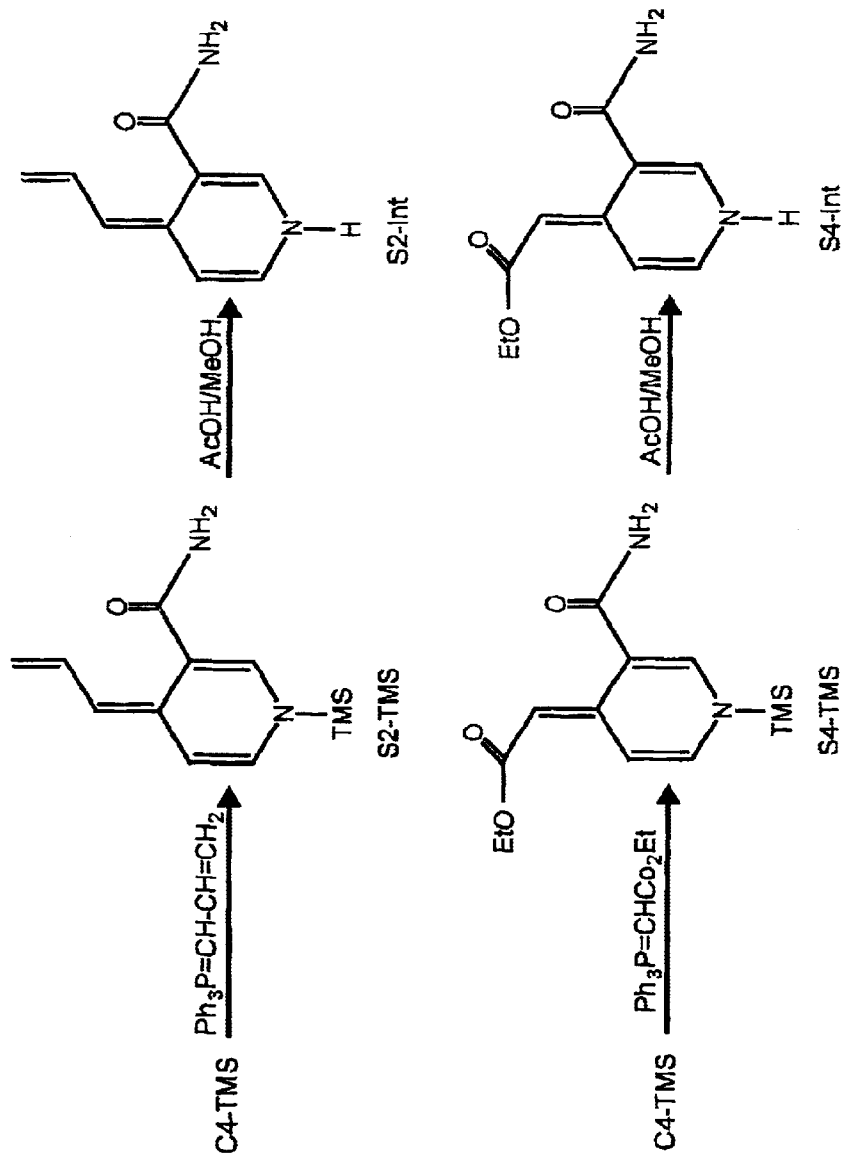

This compound was synthesized using the reaction scheme disclosed above for exo-4-methylene 2-formamide dihydropyridine, except that the Wittig reagent in this reaction was prepared by reacting 4.19 g (16.0 mmol) of triphenylphosphine and 1.92 g (16.0 mmol) of allyl bromide in 20 mL of THF and heated to reflux for 1 hr. The solution was cooled to −20° C., under a nitrogen atmosphere. One mole equivalent of LDA (lithium diisopropyl amine; 16.0 mL of 1 M LDA in THF) was slowly added over 15 minutes and warmed room temp over an additional 2 hr. This Wittig reagent was added to 3 g C4-TMS (14.0 mmol) in 20 mL tetrahydrofuran (THF), cooled to −20° C. over 20 minutes, and then warmed to room temp overnight. The reaction product was purified as described in reaction scheme 3 to yield 1.9 g (6.2 mmol) of S2-TMS; the extent of conversion was estimated by TLC analysis (where S2-TMS has an $R_f$=0.7, and S2-Int an $R_f$=0.0, using 10% ethyl acetate in hexanes with ninhydrin as the visual indicator). This synthesis is illustrated in FIG. 4C.

5. Synthesis of Exo-4-(ethylacrylate) 2-Formamide Dihydropyridine (S4-Int)

This compound was synthesized using the reaction scheme disclosed above for exo-4-methylene 2-formamide dihydropyridine, except that the Wittig reagent in this reaction (22.0 mmol in 50 mL of THF) was prepared by reacting 5.76 g (22.0 mmol) triphenylphosphine and 3.65 g (22.0 mmol) ethyl bromide acetate in 50 mL THF, as described in reaction scheme 4, followed by deprotonation with one equivalent (22.0 mmol of 1 M solution) of LDA. This Wittig reagent was added to C4-TMS (4.3 g (20.0 mmol) in 20 mL tetrahydrofuran (THF)), cooled to −20° C. over 20 minutes, then warmed to room temp overnight. The reaction product was purified as described in reaction scheme 3 above to yield 1.3 g (6.2 mmol) of S4-Int; the extent of conversion was estimated by TLC analysis (where S4-TMS has an $R_f$=0.2, and S4-Int an $R_f$=0.0 using 10% ethyl acetate in hexanes with ninhydrin as the visual indicator). This synthesis is illustrated in FIG. 4C.

6. Synthesis of Exo-4-cyclopropyl-2-formamide-dihydropridine (S3-Int)

Figure 4D:
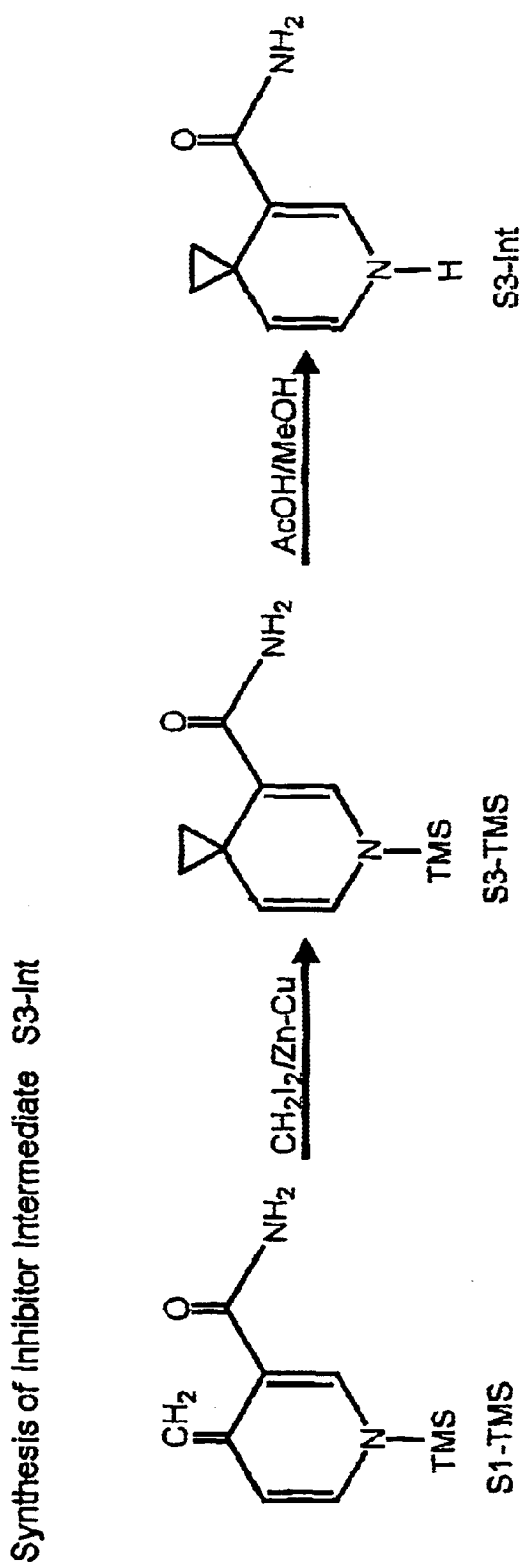

Cyclopropylization was accomplished using the Simmons-Smith procedure (Simmons et al., 1973, *Org. React.* 20: 1–131). A Zn—Cu couple (4.3 g, 34 mmol) was produced as described by LeGoff (LeGoff et al., 1964, *J. Org. Chem.* 29: 2048) and then reacted with 4.4 g (16.6 mmol) diiodomethane. This mixture was cooled to −10° C. under nitrogen atmosphere. S1-TMS (3 g, 16.6 mmol) in 20 mL dichloromethane was added and stirred for 24 h under a nitrogen atmosphere at room temperature. Water-saturated ammonium chloride (20 mL) was added, stirred and the phases separated. The organic phase dried over anhydrous sodium sulfate, filtered and purified by column chromatography as described above to yield 1.3 g (6.0 mmol) of exo-4-cyclopropyl-2-formamide-N-TMS dihydropyridine (S1-TMS). The TMS group was removed as described above to yield 0.85 g (5.7 mmol) of exo-4-cyclopropyl-2-formamide-dihydropyridine (S3-Int). The reaction product was purified as described in reaction scheme 3; the extent of conversion was estimated by TLC analysis (where S1-TMS has an $R_f$=0.8, and S1-Int an $R_f$=0.1, using 5% ethyl acetate in hexanes with ninhydrin as the visual indicator). This synthesis is illustrated in FIG. 4D.

7. Synthesis of Exo-4-epoxy-2-formamide-dihydropyridine (S5-Int)

To a 50 mL round-bottomed flask was added 3.2 g (17.8 mmol) S1-TMS and 20 mL dichloromethane. This mixture was cooled to −10° C. under nitrogen atmosphere. m-Chloroperoxybenzoic acid (5.7 g, 16.6 mmol, 50% purity; see Plesnicar, 1978, OXIDATIONS IN ORGANIC CHEMISTRY, PT. C, Academic Press: N.Y., pp. 212–252) in 10 mL dichloromethane was added and stirred at −10° C. for 3 h. Water-saturated sodium bicarbonate (20 mL) was added, the mixture stirred for 30 min at room temperature and the phases were separated. The dichloromethane phase was dried over anhydrous sodium sulfate, filtered, and purified by column chromatography as described above to yield 2.24 g (15.1 mmol) of exo-4-epoxy-2-formamide-N-TMS dihydropyridine (S5-TMS). The TMS group was removed as described above to yield 2.2 g (14.4 mmol) exo-4-epoxy-2-formamide-dihydropyridine (S5-Int). The reaction product was purified as described in reaction scheme 3; the extent of conversion was estimated by TLC analysis (where S5-TMS has an $R_f$=0.7, and S1-Int an $R_f$=0.1, using 5% ethyl acetate in hexanes with ninhydrin as the visual indicator). This synthesis is illustrated in FIG. 4B.

8. Synthesis of per-Trimethylsilyl Adenosine 5'-Diphosphate (TMS-ADP)

Figure 4E:
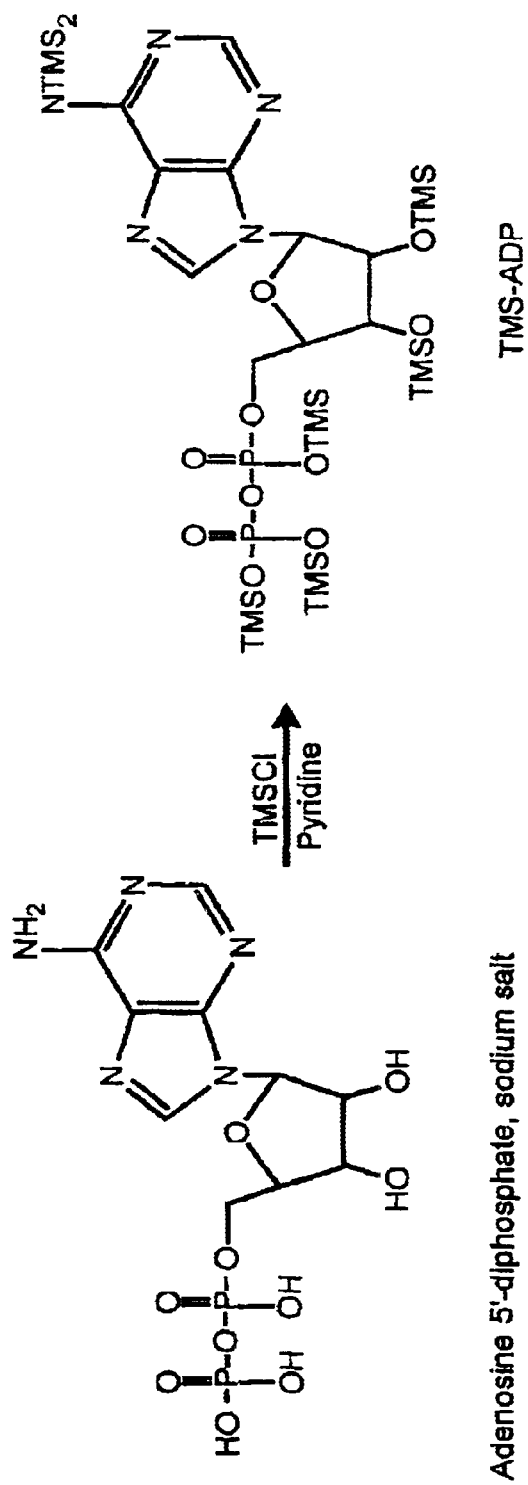

To a 500 mL round-bottomed flask was added 3 g (21.7 mmol) adenosine-5'-diphosphate sodium salt and 200 mL pyridine. After the salt had dissolved, the solution was cooled to 0° C. under nitrogen atmosphere. Trimethylsilyl chloride (85 g, 800 mmol) in 200 mL dichloromethane was added slowly to the solution. After this addition was complete, the reaction was stirred at 35° C. for 8 hr. The pyridine hydrochloride salt was removed by filtration and excess pyridine and dichloromethane removed under high vacuum for 24 hr to yield 19.3 g (21.3 mmol) of TMS-ADP. The product was used without further purification. This synthesis is illustrated in FIG. 4E.

9. Synthesis of 4-(1'3'-Propanediol-acetal)-2-formamide-dihydropyridine (C1-Int)

Figure 4F:
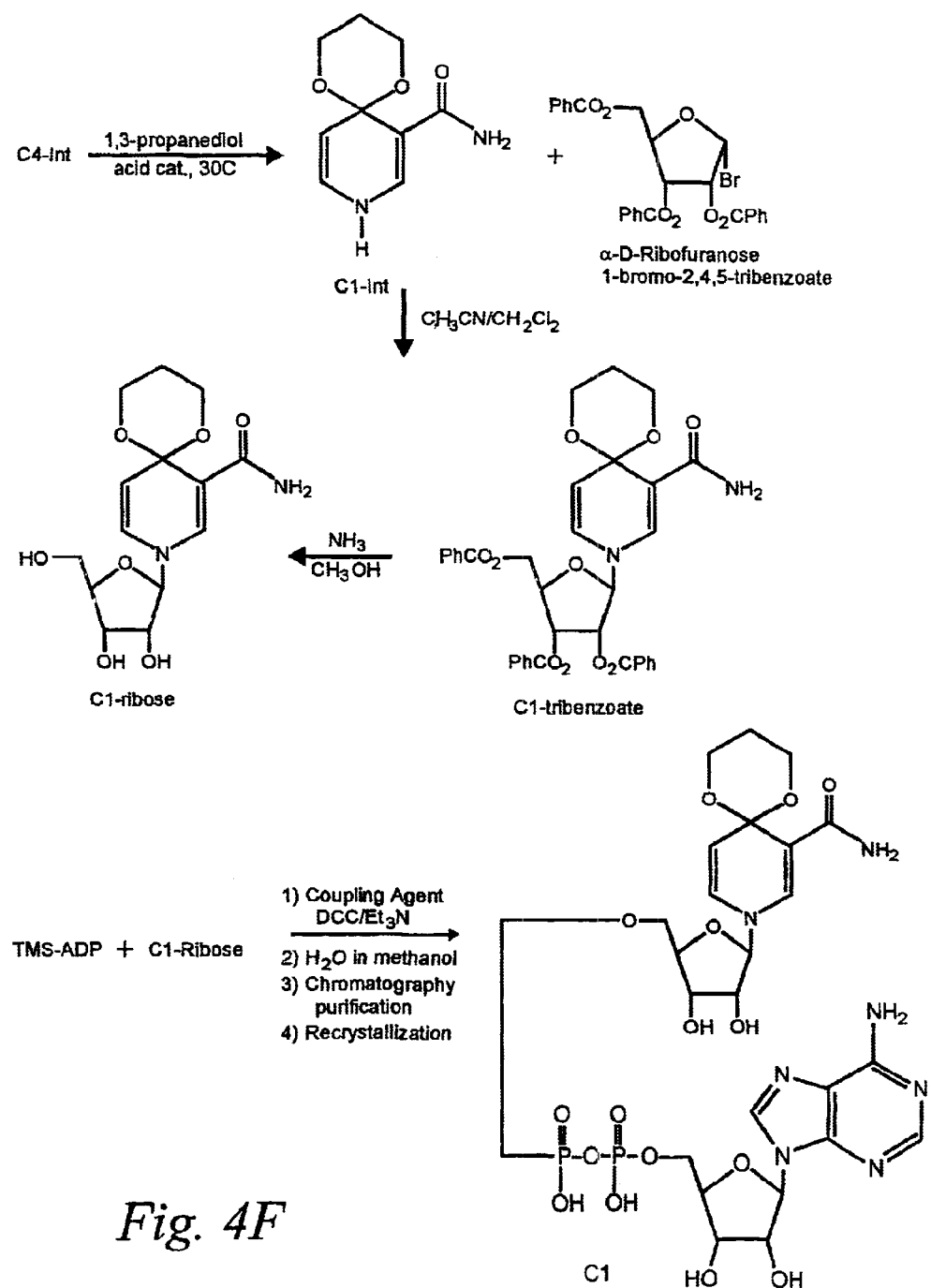

To a 50 mL round-bottomed flask was added 3 g (21.7 mmol) C4-Int 20 mL dichloromethane, 2.5 g (32.6 mmol) 1,3-propanediol and 2 g of 3 Å molecular sieves. p-Toluenesulfonic acid monohydrate (5 g, 26.3 mmol) was added and the mixture warmed to 30° C. and incubated for 24 h. The reaction mixture was filtered as described above and washed with water-saturated sodium bicarbonate (3×10 mL washes) to remove excess p-toluenesulfonic acid. The organic phase was then dried and purified by column chromatography as describe above to yield 4.0 g (21.3 mmol) C1-Int. This synthesis is illustrated in FIG. 4F.

10. Synthesis of 4-(1'3'-Propanediol-acetal)-2-formamide-dihydropyridine-NADH (C1)

To a 250 mL round-bottomed flask containing 1.4 g (7.9) C1-Int and 50 mL anhydrous acetonitrile was added 4.1 g (7.9 mmol) α-D-ribofuranose-1-bromo-2,4,5-tribenzoate (according to Howell et al., 1988, *J. Org. Chem.* 53: 85) in 50 mL anhydrous dichloromethane under nitrogen atmosphere. This solution was stirred at room temperature for 5 days. The mixture was then concentrated and C1-tribenzoate α/β isomers separated by chromatography (according to Howell et al., 1988, ibid.). β-C1-tribenzoate was deprotected with a solution of ammonia and ethanol (Howell et al., 1988, ibid.) to yield 1.1 g (3.2 mmol) C1-ribose.

To C1-ribose (1 g, 3.4 mmol) in 50 mL triethylamine was added 3.4 g (3.4 mmol) TMS-ADP (prepared as described above) in 25 mL dichloromethane and 10 mL triethylamine. This mixture was stirred at −10° C. under nitrogen atmosphere for 1 hr. 1,3-Dicyclohexylcarbodiimide (0.7 g, 3.4 mmol) in 10 mL dichloromethane was added to this mixture dropwise and the reaction allowed to warm to room temperature overnight under nitrogen. Excess triethylamine and dichloromethane was removed under reduced pressure to produce a syrup that was dissolved in a solution of 200 mL methanol an 3 mL water. This mixture was then stirred for 12 h at room temperature to remove the TMS protecting group. The methanol was removed under high vacuum for 8 hr, and the residue dissolved in 10 mL water. Product was purified by ion-exchange chromatography according to Howell et al. (1988, *J. Org. Chem.* 53: 85). Fractions containing C1 were identified by an observed increase in absorbency at 340 nm; these fractions were collected and lyophilized. The solid material was dissolved in a minimal amount of water and then ethanol was added until the solution became cloudy. This mixture was then placed at −20° C. for 4–7 days. The crystals formed thereby were collected by filtration, dried and weighed to yield 0.57 g (0.71 mmol). The product was stored at −20° C. under nitrogen and protected from light (e.g., in brown bottles) until use. This synthesis is illustrated in FIG. 4F.

11. Synthesis of 4-Oxo-2-formamide-dihydropyridine NADH (C4)

The title compound was produced as described in Synthesis 10, except that C4-Int was substituted for C1-Int. C4-Int 1.5 g (10.9 mmol) and 5.65 g (10.9 mmol) α-D-ribofuranose-1-bromo-2,4,5-tribenzoate were used and yielded 0.63 g (0.70 mmol) of C4 after purification and recyrstallization.

12. Synthesis of Exo-4-methylene 2-Formamide-dihydropyridine NADH (S1)

The title compound was produced as described in Synthesis 10, except that S1-Int was substituted for C1-Int. S1-Int 1.3 g (9.3 mmol) and 4.80 g (9.3 mmol) α-D-ribofuranose-1-bromo-2,4,5-tribenzoate were used in the reaction and yielded 0.21 g (0.20 mmol) of S1 product after purification and recyrstallization.

13. Synthesis of Exo-4-(1'3'-butadiene) 2-Formamide-dihydropyridine NADH (S2)

The title compound was produced as described in Synthesis 10, except that S2-Int was substituted for C1-Int. S2-Int 2.57 g (11.0 mmol) and 5.7 g (11.0 mmol) α-D- ribofuranose-1-bromo-2,4,5-tribenzoate were used in the reaction and yielded 0.45 g (0.5 mmol) of S2 product after purification and recyrstallization.

14. Synthesis of Exo-4-(cyclopropyl) 2-Formamide-dihydropyridine NADH (S3)

The title compound was produced as described in Synthesis 10, except that S3-Int was substituted for C1-Int. S3-Int 1.57 g (10.5 mmol) and 5.43 g (10.5 mmol) α-D-ribofuranose-1-bromo-2,4,5-tribenzoate were used in the reaction and yielded 0.72 g (0.78 mmol) of S3 product after purification and recyrstallization.

15. Synthesis of Exo-4-(ethyl acrylate) 2-Formamide-dihydropyridine NADH (S4)

The title compound was produced as described in Synthesis 10, except that S4-Int was substituted for C1-Int. S4-Int (1.63 g, 8.0 mmol) and 4.14 g (8.0 mmol) α-D-ribofuranose-1-bromo-2,4,5-tribenzoate were used in the reaction and yielded 0.53 g (0.57 mmol) of S4 product after purification and recyrstallization.

16. Synthesis of Exo-4-(epoxy) 2-Formamide-dihydropyridine NADH (S5)

The title compound was produced as described in Synthesis 10, except that S5-Int was substituted for C1-Int. S5-Int 1.4 g (9.3 mmol) and 4.80 g (9.3 mmol) α-D-ribofuranose-1-bromo-2,4,5-tribenzoate used in the reaction and yielded 0.19 g (0.2 mmol) of S5 product after purification and recyrstallization.

17. Synthesis of 4,4-Dimethyl-2-formamide-dihydropyridine (C2-Int)

Figure 4G:
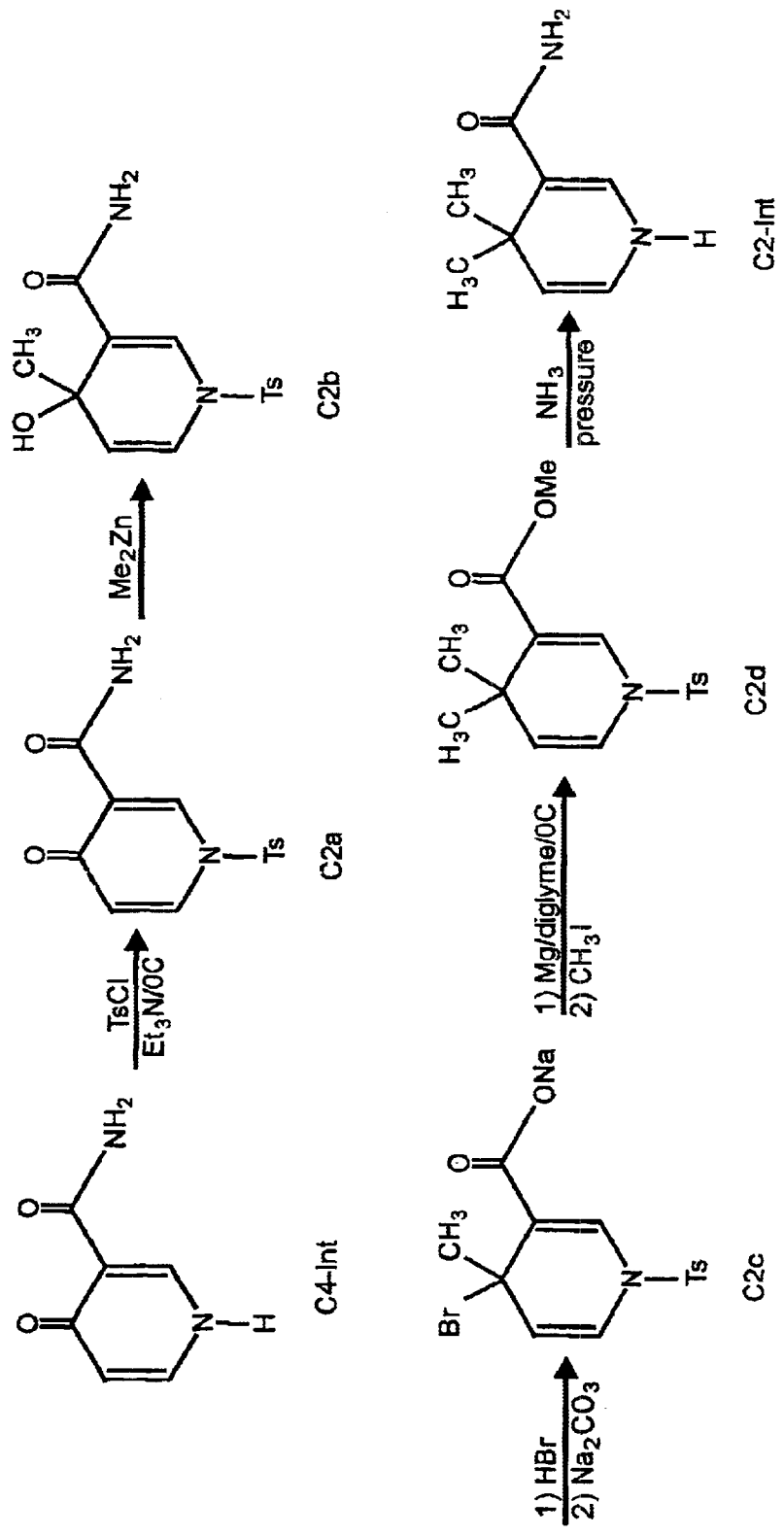

To a 50 mL round-bottomed flask was added 3 g (21.7 mmol) C4-Int, 20 mL dichloromethane and 10 mL triethylamine and the mixture cooled to 0° C. p-Toluenesulfonyl chloride (4.1 g, 21.7 mmol) in 20 mL dichloromethane was added dropwise and the mixture warmed to room temperature with stirring and incubated for 24 h. The reaction mixture was then concentrated under reduced pressure. The residue was dissolved in 100 mL toluene and sequentiually washed once with 10 mL 1N HCl and once 10 mL water-saturated sodium bicarbonate. The organic phase was dried and purified by column chromatography as described above in Synthesis 2 to yield 6.16 g (21.0 mmol) of C2a. This synthesis is illustrated in FIG. 4G.

To a 50 mL round-bottomed flask was added 2 g (6.8 mmol) C2a and 20 mL anhydrous THF, and the mixture cooled to 0° C. under nitrogen atmosphere. Dimethylzinc (6.8 mL of a 1M solution in heptane, 6.8 mmol) was added and stirred at 0° C. for 4 h. Methanol (5 mL) followed by 2 mL water were then added and the solution concentrated under reduced pressure. The residue was dissolved in 100 mL dichloromethane and washed with 10 mL 1N HCl and 10 mL water-saturated sodium bicarbonate. The organic phase was dried with anhydrous sodium sulfate, filtered and concentrated to yield 2.06 g (6.7 mmol) of product. This product used in the next synthetic reaction without further purification. This reaction product, termed 2Cb herein, is shown in FIG. 4G.

Hydrogen bromide in acetic acid (13.6 mL of a 30 wt% solution) was added slowly to the 2Cb product of the above reaction at −10° C. The mixture was stirred at −10° C. for 2 h and then carefully neutralized with solid sodium carbonate. The mixture was washed with 10 mL 1N HCl and 10 mL water-saturated sodium bicarbonate. The organic phase was dried with anhydrous sodium sulfate, filtered and purified by recrystallizing from ethyl acetate and hexanes to yield 1.1 g (3.1 mmol) product. This reaction product, termed C2c herein, is shown in FIG. 4G.

C2c (1 g, 2.7 mmol) in 5 mL 2-methoxyethyl ether (diglyme) was added slowly to 2 g activated magnesium in 10 mL diglyme at 0° C. The mixture was stirred at 0° C. for 24 h and then excess magnesium removed by decanting. Methyl iodide (0.85 g, 6 mmol) was added and the mixture warmed to 45° C. for 20 h. The resulting product, termed C2d herein and illustrated in FIG. 4G, was washed twice with 10 mL 1N HCl and 10 mL water-saturated sodium bicarbonate The organic phase was dried and purified by column chromatography as described above to yield 0.41 g (1.3 mmol) of C2d.

Finally, the tosyl protecting group was removed as follows. C2d (0.41 g, 1.3 mmol) was dissolved in 10 mL methanol in a 125 mL high pressure flask. Anhydrous ammonia was added under conditions wherein the pressure was maintained at 75 psi at a temperature of 90° C.; this mixture was incubated for 48 h. After the incubation was complete, excess ammonia was safely vented and the product, C2-Int was purified by column chromatography to yield 0.14 g (0.9 mmol). This reaction scheme and product are shown in FIG. 4G.

18. Synthesis of 4,4-Dimethyl 2-Formamide-dihydropyridine NADH (C2)

The title compound was produced as described in Synthesis 10, except that C2-Int was substituted for C1-Int. C2-Int (0.14 g, 0.9 mmol)) and 0.48 g (0.93 mmol) (α-D-ribofuranose-1-bromo-2,4,5-tribenzoate were used in the reaction and 0.052 g ($5.8 \times 10^{-5}$ mol) of C2 product after purification. This product could not be recrystallized.

19. Synthesis of 2-Formamide-dihydromorpholine (C3-Int)

Figure 4H:
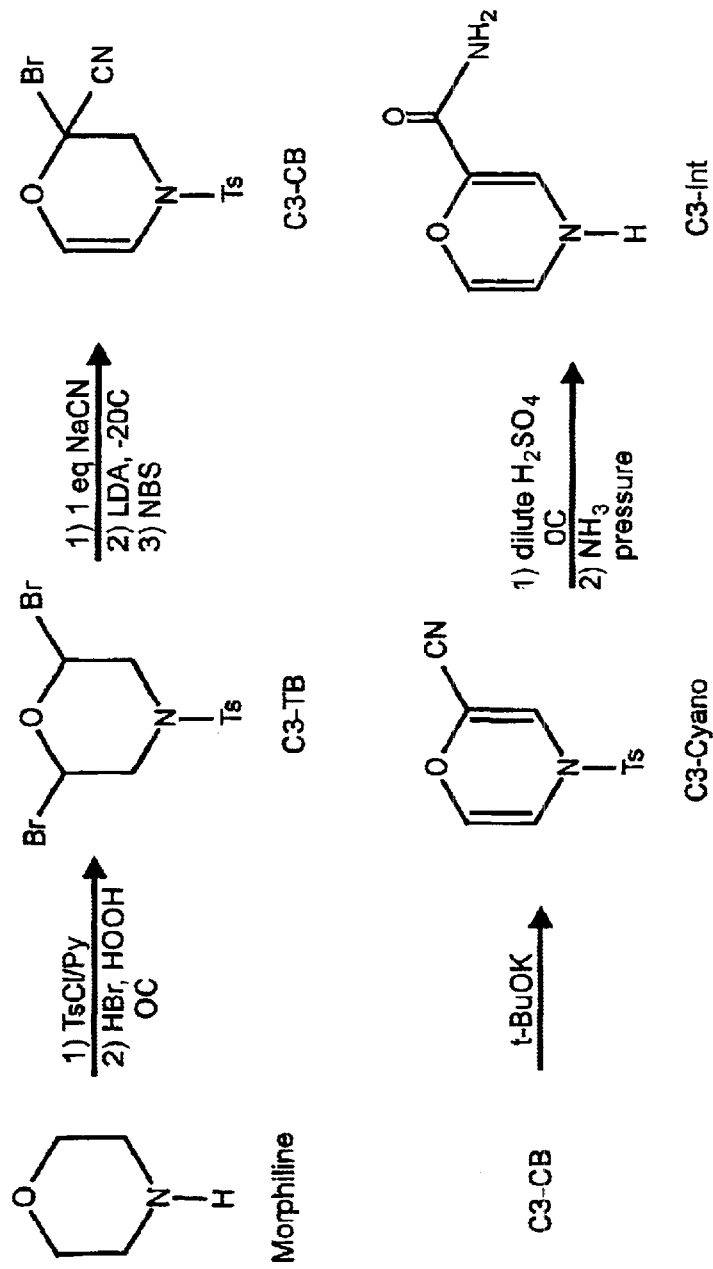

To a 50 mL round-bottomed flask was added 1.9 g (21.7 mmol) morpholine, 20 mL dichloromethane and 10 mL triethylamine, and the mixture cooled to 0° C. p-Toluenesulfonyl chloride (4.1 g, 21.7 mmol) in 20 mL dichloromethane was added dropwise and the mixture warmed to room temperature with stirring and incubated for 24 h. The reaction mixture was then concentrated under reduced pressure. The residue was dissolved in 100 mL toluene and sequentially washed once with 10 mL 1N HCl and once with 10 mL water-saturated sodium bicarbonate. The organic phase was dried to yield 5.42 g (21.7 mmol) of product. This product, N-tosyl morpholine was used without further purification. This synthesis is illustrated in FIG. 4H.

The N-tosyl morpholine produced above (3.2 g, 13.2 mmol) was added to 50 mL of ice-cold isopropyl alcohol containing 6.7 mL of 2M HBr in acetic acid and 5mL of 30 wt% hydrogen peroxide. The reaction was stirred at 0° C. for 18 hr. The reaction product was purified by adding 50 mL of hexanes and sequentially washing the organic layer once with 10 mL 1N HCl and once with 10 mL water-saturated sodium bicarbonate. Sodium thiosulfite (100 mL of 1 M in water) was used to remove residual peroxide. The organic phase was dried with anhydrous sodium sulfate and filtered as described above to yield 2.52 g (6.3 mmol) of C3-TB.

C3-TB (2.52 g, 6.3 mmol) was dissolved in 50 mL of a 1:1 mixture of isopropanol and water. To this mixture was added 1.0 g (20.4 mmol) sodium cyanide and stirred at room temperature for 1 h. The solution was concentrated, diluted with 30 mL of ether, washed with water and the organic layer dried with anhydrous sodium sulfate. The solution was concentrated and diluted with 50 mL THF and then cooled to −20° C. under a nitrogen atmosphere. Lithium diisopropylamide (40 mL of a 1M solution in THF) was added dropwise and stirred at −20° C. for 30 min. The reaction was quenched by the addition of 3.78 g (20 mmol) N-bromosuccinimide in 20 mL THF. This mixture was then stirred at 0° C. for 3 h. The mixture was sequentially washed once with 10 mL 1N HCl and once with 10 mL water-saturated sodium bicarbonate. The product, termed C3-CB herein and illustrated in FIG. 4H, was purified by column chromatography as described above to yield 1.48 g (4.28 mmol) of product; the extent of purification was estimated by TLC analysis (where C3-CB has an $R_f$=0.5 in hexanes with UV light as the visual indicator.

C3-CB (1.48 g, 4.28 mmol) was dissolved in 50 mL isopropanol, cooled to 0° C. under nitrogen atmosphere, and potassium t-butoxide (5 mL of a 1M solution in t-butanol) added dropwise. The mixture was stirred at 0° C. for 30 min and concentrated under reduced pressure. Sulfiric acid (50 mL of a 1M solution) was added to the residue and stirred at 0° C. for 3 days. The mixture was neutralized with sodium bicarbonate until the pH was 7–8 (determined using pH paper) and continuously extracted with 100 mL ether for 2 days The ether was then dried over anhydrous sodium sulfate, filtered and concentrated under reduced pressure. The tosyl protecting group was removed as described in the synthesis of C2-Int above, and C3-Int product purified by column chromatography to yield 0.19 g (1.5 mmol) of product; the extent of purification was estimated by TLC analysis (where C3-CB has an $R_f$=0.1 in 2% acetic acid in tert-butyl methyl ether with sulfuric acid/heat as the visual indicator). This reaction scheme is shown in FIG. 4H.

20. Synthesis of 2-Formamide-dihydromorpholine NADH (C3)

The title compound was produced as described in Synthesis 10, except that C3-Int was substituted for C1-Int. C3-Int (0.14 g, 0.93 mmol) and 0.48 g (0.93 mmol) α-D-ribofuranose-1-bromo-2,4,5-tribenzoate were used in the reaction to yield 0.01 g (1.3×10$^{-5}$ mol) of S5 product after purification. This material could not be recrystallized.

21. Synthesis of 4,4-Dimethyl-2-formamide-dihydropyridine NADH (C5)

To a 100 mL round-bottomed flask containing 10 g (53.2 mmol) 3-bromo-1-formamide-1,3-cyclohexadiene and 55 mL anhydrous THF was added 10.1 g (159 mmol) activated zinc. This mixture was warmed to 40° C. with stirring for 48 h under a nitrogen atmosphere. The solution was decanted from excess zinc and added dropwise to a solution of 27.9 g (53.2 mmol) α-D-ribofuranose-1-bromo-2,4,5-tribenzoate (according to Howell et al., 1988, J. Org. Chem. 53: 85) in 100 mL anhydrous dichloromethane at −10° C. under nitrogen atmosphere. This solution was stirred at −10° C. for 6 h. This mixture was then poured into 200 mL ether and washed with 50 mL water-saturated ammonium chloride. The phases were separated and C5-tribenzoate α/β isomers separated by chromatography (according to Howell et al., 1988, ibid.). β-C5-tribenzoate was deprotected with a solution of ammonia and ethanol (Howell et al., 1988, ibid.) to yield 3.12 g (12.2 mmol) of C5-ribose.

Figure 4I:
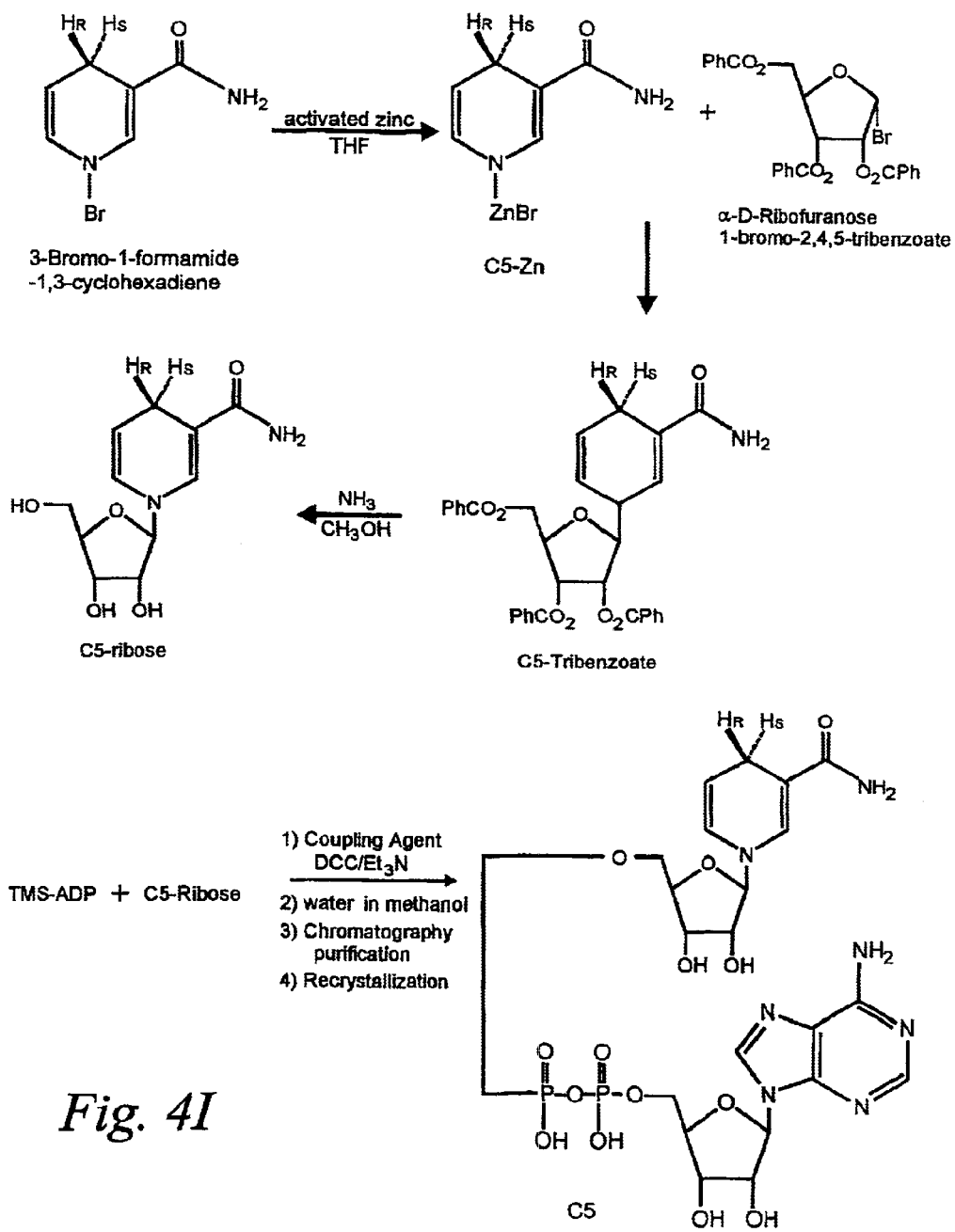

To C5-ribose (1 g, 3.9 mmol) in 50 mL triethylamine was added 3.9 g (3.9 mmol) TMS-ADP in 25 mL triethylamine. This mixture was stirred at −10° C. under nitrogen atmosphere 1 hr. 1,3-Dicyclohexylcarbodiimide (0.8 g, 3.9 mmol) in 10 mL dichloromethane was added to this mixture dropwise and the reaction allowed to warm to room temperature overnight under nitrogen. Excess triethylamine and dichloromethane was removed under reduced pressure to produce a syrup that was dissolved in a solution of 200 mL methanol an 3 mL water. This mixture was then stirred for 12 h at room temperature to remove the TMS protecting group. The methanol was removed under reduced pressure, and the residue dissolved in 10 mL water. Product was purified by ion-exchange chromatography as described above, and fractions containing C5 were identified, collected and lyophilized. The solid material was dissolved in a minimal amount of water and then ethanol was added until the solution became cloudy. This mixture was then placed at −20° C. for 4–7 days. The crystals formed thereby were collected by filtration and dried to yield 0.42 g (0.47 mmol) of C5. The product was stored at −20° C. under nitrogen and protected from light (e.g., in brown bottles) until use This synthesis is illustrated in FIG. 4I.

22. Synthesis of Isonicotinic Acid NADH (C6)

Figure 4J:
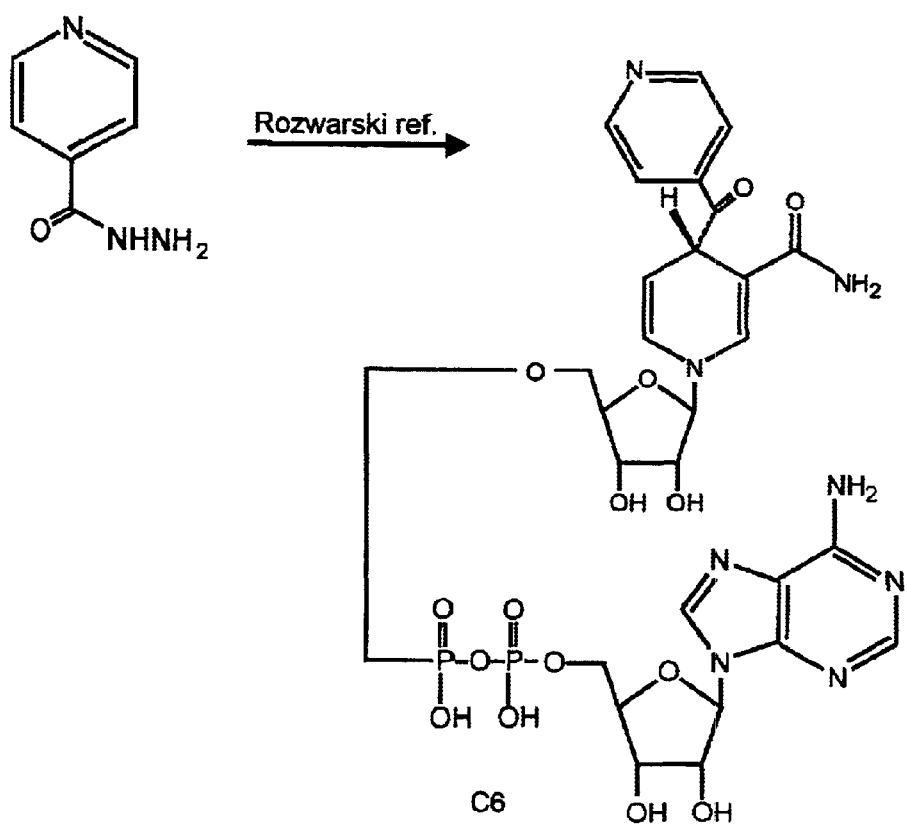

The title compound was produced as described in Rozwarski et al. (1998, Science 279: 98). The reaction scheme is shown in FIG. 4J.

EXAMPLE 3

Preparing Isoniazid-NAD Analogue Prodrugs

Activated anti-mycobacterial compounds as disclosed in Examples 1 and 2 are modified to prodrugs that are specifically activated in Mycobacterium-infected cells as follows, using INA as a specific example of the method. These compounds are shown in FIG. 2. 100 mg (0.10 mmol) of INA is dissolved in 10 mL of anhydrous pyridine, and 1.0 g (23.3 mmol) of cyanic acid (Linard, 1938; Merck Index, 1983) bubbled into the reaction mixture over 30 minutes, then stirred for 4 hr at 60° C. Excess pyridine is removed under high vacuum, then purified by HPLC, as described above. The resulting INA derivative has a urea functional group covalently linked to the 1-amino group of the adenine portion of the NAD component of INA (termed INA prodrug 1). This compound is characterized by $^1$H NMR, $^{13}$C NMR, and fast atom bombardment/mass spectrometry (FAB MS).

Alternatively, 100 mg (0.10 mmol) of INA is dissolved into 10 mL of anhydrous pyridine and cooled to 0° C. under nitrogen. Trimethylsilyl chloride (TMSCl; 5 g, 44.6 mmol) is added over 15 minutes, followed by stirring overnight at room temp. The excess TMSCl and pyridine are removed under high vacuum. Anhydrous tetrahydrofuran (THF; 20 mL) is added and the pyridine-HCl salt is removed by filtration. The THF fraction is cooled to −78° C., THF is added to keep the per TMS-INA in solution. N-Butyl lithium (1.0 mL of 0.10 M solution) is added dropwise followed by the addition of 1.0 g (23.3 mmol) of cyanic acid (Linard, 1938; Merck Index, 1983) that is bubbled into the reaction mixture over 30 minutes. The reaction is warmed and incubated at room temperature overnight. The derivatized product is isolated by the addition of 1.0 mL of water in 5 mL of ethanol, stirring at room temp for 3 hr, concentrating the reaction mixture and purifying the product by HPLC as described above. The resulting INA derivative has a urea functional group covalently linked to the nicotinamide formamide group (termed INA prodrug 2). This compound is characterized by $^1$H NMR, $^{13}$C NMR, and FAB MS.

EXAMPLE 4

Analysis of Isoniazid-NAD Analogue Prodrugs

Prodrug forms of activated anti-mycobacterial compounds as disclosed in Example 3 are tested to demonstrate Mycobacteria-specific activation of said prodrugs, using the urea-derivatized INA compounds of Example 3 as a specific example of the method.

Because the pyridine nucleotide binding site is highly conserved evolutionarily, it is expected that an inhibitor of a NAD-dependent bacterial enzyme is likely to inhibit mammalian NAD-dependent enzymes as well. Commercially-available bacterial alcohol dehydrogenase (ADH) is assayed by the method of Zahlten (1980, Biochem. Pharmacol. 29: 1973–6) in the presence of the INA to determine a $K_i$ for the compound. To control for unexpected effects on the 340 mn absorbance by the analogs, these results are verified using a calorimetric assay according to Fibla and Gonzalez-Duarte (1993, *J. Biochem. Biophys Methods* 26: 87–93). An unrelated enzyme, NADH-dependent glutamate dehydrogenase is assayed according to the method of Meredith and Schmidt (1991, *Life Sci. Adv. Plant Physiol.* 10: 67–71) to confirm the ADH-derived results on the inhibitory potential of these analogs. The experiments described above will be repeated with urea-modified NAD analogs. These compounds should not have inhibitory activity, due to the alteration of portions of the compound that interact with the NAD binding site of the enzymes.

Implicit in the proposed mechanism of anti-tubercular activity of these prodrugs is that the mammalian cell, most preferably phagocytic cells such as macrophages, remains functional and intact long enough for the NAD analog prodrugs to kill the infecting mycobacterium. It is therefore essential to understand the degree of inhibition of NADPH-dependent enzymes as well, since these are the mainly biosynthetic enzymes required for macrophage repair. The NADPH-dependent enzymes isocitrate dehydrogenase (Dedhia et al., 1979, *Experimental Mycology* 3: 229–239) and malic enzyme (Mackall & Meredith, 1970, *Anal. Biochem.* 95: 270–4) are used to examine the effects of the INA derivatives on NADP-utilizing enzymes.

The ability of bacterial urease to produce active enzyme inhibitors is tested by in vitro incubation of the urea-modified NAD analogs with urease, both commercially obtained purified enzyme and partially purified bacterial urease obtained for these experiments. Urease release of inhibitors is evaluated in two ways. During incubation of the urea-modified analogs with urease under assay conditions, the release of the unmodified NAD analog is monitored by HPLC (Anderson & Anderson, 1983, *Anal. Biochem.* 134: 50–5), a method used successfully to quantitate a number of NAD analogs. Secondly, the ability to generate enzyme inhibition in the test systems (ADH, GDH) after incubation is tested and comprises the most compelling evidence that urease can activate the urea-derivatized NAD analogues of the invention.

To demonstrate that urease cleaves the urea functional groups on INA prodrug 1 and INA prodrug 2 to yield INA, urease (urea amidohydrolase [EC 3.5.1.5]) from *M. tuberculosis* (Clemens et al., 1995, *J. Bacteriol.* 177: 5644–52), *M. fortuitum, M. chelonae,* and *Proteus vulgaris* are tested as follows.

Urease activity is measured by coupling with ammonia production, from urea hydrolysis, to a glutamate dehydrogenase (GDH) reaction (as described in the Worthington Handbook, 1994). The decrease in NADH concentration (measured spectrophotometrically at 340 nm) is proportional to the amount of glutamate formed from ammonia, which is produced by hydrolysis of urea. The concentration of the prodrug and INA are also monitored by HPLC.

It should be understood that the foregoing disclosure emphasizes certain specific embodiments of the invention and that all modifications or alternatives equivalent thereto are within the spirit and scope of the invention as set forth in the appended claims.

What is claimed is:

1. An antimycobacterial compound comprising an inhibitor of a mycobacterium-specific enzyme, wherein the compound has the formula:

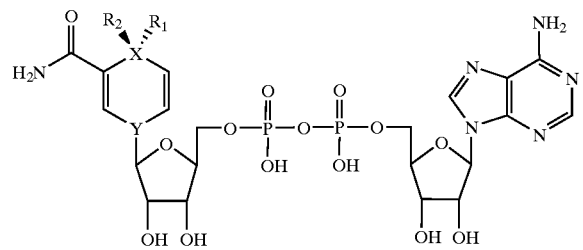

wherein X is C or O;

Y is N or C;

R1 and R2 are independently absent or H, $CH_3$, or $CH_2\text{-}CH_3$, or together are $=CH_2,O(CH_2)+\!-\!CH_2\!-\!CH_2\!-\!$, $=CH\!-\!CH\!=\!CH_2$, $=CH\!-\!COOCH_2\!-\!CH_3$, $-\!CH_2\!-\!(CH_2)_3\!-\!CH_2\!-\!$ or $OCH_2$.

2. The compound of claim 1, wherein X is C, Y is N and R1 and R2 are together pentyl, and the nicotinamide portion of the compound has the structure:

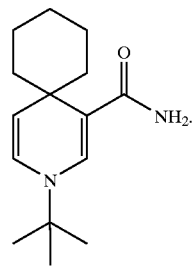

3. The compound of claim 1, wherein X is C, Y is N and each of R1 and R2 are methyl, and the nicotinamide portion of the compound has the structure:

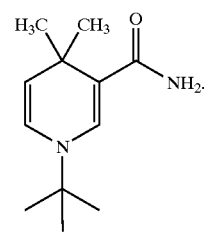

4. The compound of claim 1, wherein X is O, Y is C and R1 and R2 are absent, and the nicotinamide portion of the compound has the structure:

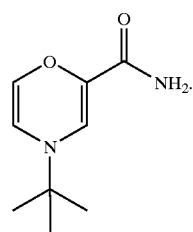

5. The compound of claim 1, wherein X is C, Y is N and R1 and R2 are each H, and the nicotinamide portion of the compound has the structure:

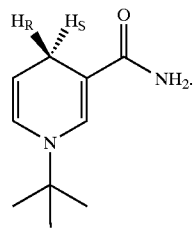

6. The compound of claim 1, wherein X is C, Y is O and R1 and R2 are together =CH$_2$, and the nicotinamide portion of the compound has the structure:

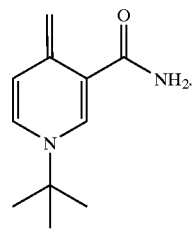

7. The compound of claim 1, wherein X is C, Y is N and R1 and R2 are together =CH—CH=CH$_2$, and the nicotinamide portion of the compound has the structure:

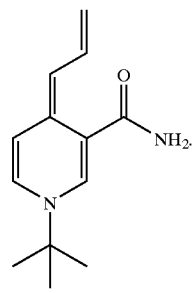

8. The compound of claim 1, wherein X is C, Y is N and R1 and R2 are together —CH$_2$—CH$_2$—, and the nicotinamide portion of the compound has the structure:

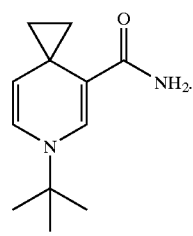

9. The compound of claim 1, wherein X is C, Y is N and R1 and R2 are together =CH—COOCH$_2$—CH$_3$, and the nicotinamide portion of the compound has the structure:

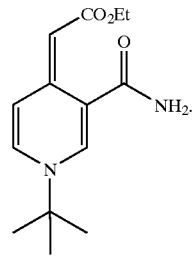

10. The compound of claim 1, wherein X is C, Y is N and R1 and R2 are together —O—CH$_2$—, and the nicotinamide portion of the compound has the structure:

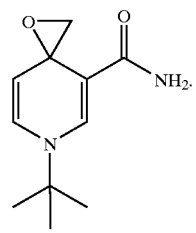

11. A composition of matter comprising the compound of any one of claims 1 through 10 wherein the compound is derivatized by covalently linking a derivatizing group on a portion of the compound required for binding to an NAD-requiring enzyme.

12. A composition of matter according to claim 11, wherein the derivatizing group is a urea moiety.

13. A composition of matter according to claim 12, wherein the derivatized portion of the compound is the formamide group of the nicotinamide component thereof or and 1-amino group of the adenine component thereof.

14. A pharmaceutical composition comprising the compound of claim 12 and a pharmaceutically acceptable carrier.

15. A method of treating an animal infected with a disease-causing microorganism of a Mycobacterium species, the method comprising the step of administering to the animal a therapeutically effective amount of a pharmaceutical composition of claim 14.

16. A method of killing a microorganism infecting a mammalian cell, the method comprising contacting said cell with the composition of claim 12.

17. A method of killing a tuberculosis-causing microorganism infecting a mammalian cell, the method comprising contacting said cell with the composition of claim 12.

* * * * *